United States Patent [19]

Pettipher et al.

[11] Patent Number: 5,482,944
[45] Date of Patent: Jan. 9, 1996

[54] PYRIMIDONES AND IMIDAZOLINONES FOR TREATMENT OF SHOCK

[75] Inventors: Eric R. Pettipher, Norwich; Victoria L. Cohan, Groton, both of Conn.

[73] Assignee: Pfizer Inc., New York, N.Y.

[21] Appl. No.: 91,693

[22] Filed: Jul. 13, 1993

[51] Int. Cl.$^6$ ...................... A61K 31/505; A61K 31/415
[52] U.S. Cl. ............................................ 514/274; 514/392
[58] Field of Search ..................................... 514/274, 392, 514/274

[56] References Cited

U.S. PATENT DOCUMENTS 4,582,834  4/1986  Stenzel ..................................... 514/274
4,971,959  11/1990  Hawkins ................................. 514/150

FOREIGN PATENT DOCUMENTS 9107501  5/1991  WIPO .
9107178  5/1991  WIPO .
9207567  5/1992  WIPO .

OTHER PUBLICATIONS

Semmler et al., Immunology, 78, 520–525 (1993).

*Primary Examiner*—Jerome D. Goldberg
*Attorney, Agent, or Firm*—Peter C. Richardson; Paul H. Ginsburg; Gezina Holtrust

[57] ABSTRACT

The compounds of the formula

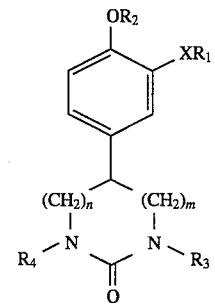

and the pharmaceutically acceptable acid addition salts thereof, wherein X, m, n, $R_1$, $R_2$, $R_3$ and $R_4$ are as defined herein are useful in the treatment of shock and other TNFα-related disorders.

2 Claims, No Drawings

PYRIMIDONES AND IMIDAZOLINONES FOR TREATMENT OF SHOCK

BACKGROUND OF THE INVENTION

This invention relates to a method for the treatment of shock and for inhibition of production of tumor necrosis factor alpha (TNFα) in a mammal by use of certain pyrimidones and imidazolinones.

The pyrimidones and imidazolinones of use in the present invention are disclosed in U.S. Pat. No. 5,128,358, which is incorporated by reference, for use as antidepressants. WO 91/07178 discloses the use of these compounds in the treatment of asthma, and inflammatory and skin diseases. The use of these compounds in the treatment of shock and inhibition of TNFα is not disclosed in these references.

SUMMARY OF THE INVENTION

According to the invention, production of TNFα is inhibited by administering to a subject in need of such inhibition a compound of the formula

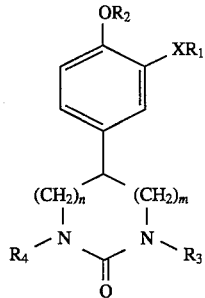

or a pharmaceutically acceptable acid addition salt of said compound having a basic nitrogen atom, wherein X is O or NH;

m is 0, 1 or 2;

n is 0, 1 or 2;

m and n is 1 or 2;

$R_1$ is $C_7$–$C_{11}$ tricycloalkyl or $C_7$–$C_{11}$ bicycloalkyl;

$R_2$ is methyl or ethyl;

$R_3$ is hydrogen, $C_1$–$C_3$ alkyl, $C_2$–$C_3$ alkenyl, benzyl or phenethyl; and $R_4$ is hydrogen, $C_1$–$C_3$ alkyl or $C_2$–$C_3$ alkanoyl; with the proviso that when m+n is 1 then m is 0 and n is 1, and with the proviso that when m+n is 2 then $R_3$ and $R_4$ are each hydrogen, in an amount sufficient for said treatment.

In a preferred method, the compound used is 5-(3-[(2S)-exobicyclo[2.2.1]hept-2-yloxy]-4-metholxyphenyl)-3,4,5,6-tetrahydropyrimidin-2(1H)-one.

In a more specific embodiment of the invention, the compound of formula I as defined above is used in the treatment of shock.

DETAILED DESCRIPTION OF THE INVENTION

The compounds or formula I and the pharmaceutically acceptable acid addition salts thereof (the active compounds) and their preparation are disclosed in U.S. Pat. No. 5,128,358. As disclosed in the patent, stereocenters exist in several of the polycycloalkyl groups $R_1$ and the pyrimidinone or imidazolidinone groups. The racemic-diastereomeric structures and the individual optical isomers are also included in the compounds of formula I of use in the method of the invention.

The active compounds inhibit production of TNFα and are therefore of use in the treatment of diseases associated with excessive or unregulated TNFα production such as septic shock, hemorrhagic shock, rheumatoid arthritis, insulin resistance in type 2 diabetes, inflammatory diseases, adult respiratory distress syndrome, asthma, post-renal dialysis syndrome, and graft versus host disease after bone marrow transplantation.

As used herein, treatment includes both the prevention and the alleviation of a disease.

The active compound may be administered to a subject in need of treatment by a variety of conventional routes of administration, including orally, parenterally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The active compound may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the active compound and the pharmaceutically acceptable carriers are then readily administered in a variety of dosage forms such as tablets, powders, lozenges, syrups, injectable solutions and the like.

These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerine and combinations thereof.

For parenteral administration, solutions of the active compound in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques.

The ability of an active compound to inhibit production of TNFα is demonstrated as follows.

EXAMPLE

Endotoxic shock was induced in male Balb/c mice (20–25 g) by the intraperitoneal injection of 0.3 mg lipopolysaccharide (*E. coil*, 0111:B4) and survival monitored at intervals up to 72 hours. Drug was delivered by oral gavage in 0.5% carboxy methylcellulose vehicle 0.5 hours before the induction of endotoxic shock.

Serum was removed from Balb/c mice 1 hour after intraperitoneal administration of 0.3 mg lipopolysaccharide (*E. coil*, 0111:B4) and assayed for TNFα by ELISA (Genzyme, Boston, Mass.). Drug was delivered by oral garage in 0.5% carboxymethyl cellulose vehicle 0.5 hours before injection of lipopolysaccharide.

Mononuclear cells were isolated from human peripheral blood by Ficoll/Hypaque and adhesion to polystyrene plates. Adherent cells were incubated for 1 hour at 37° C. with 5-(3-[(2S)-exobicylo[2.2.1]hept-2-yloxy]-4-methoxyphenyl)-3,4,5,6-tetrahydropyrimidin-2(1H)-one prior to stimulation with LPS (10 ng/ml) for 18 hours. TNFα release was assessed in diluted culture supernatants using a sandwich ELISA (R&D, Minneapolis, Minn.).

It was found that 5-(3-[(2S)-exobicylo[2.2.1]hept-2-yloxy]-4-methoxyphenyl)-3,4,5,6-tetrahydropyrimidin-2(1H)-one inhibited (1) mortality and TNFα production in murine endotoxic shock (ED50=4.1 mg/kg p.o.), and (2) TNFα release from human monocytes in vitro (IC50= 0.12±0.05 μpm, n=4).

We claim:

1. A method for the treatment of septic shock, hemorrhagic shock, rheumatoid arthritis, insulin resistance in type 2 diabetes, adult respiratory distress syndrome, post-renal dialysis syndrome, and graft versus host disease after bone marrow transplantation, which comprises administering to a subject in need of such treatment a compound of the formula

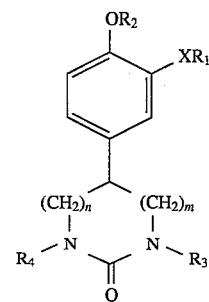

or a pharmaceutically acceptable acid addition salt of said compound having a basic nitrogen atom, wherein X is O or NH;

m is 0, 1 or 2;

n is 0, 1 or 2;

m and n is 1 or 2;

$R_1$ is $C_7$–$C_{11}$ tricycloalkyl or $C_7$–$C_{11}$ bicycloalkyl;

$R_2$ is methyl or ethyl;

$R_3$ is hydrogen, $C_1$–$C_3$ alkyl, $C_2$–$C_3$ alkenyl, benzyl or phenethyl; and $R_4$ is hydrogen, $C_1$–$C_3$ alkyl or $C_2$–$C_3$ alkanoyl; with the proviso that when m+n is 1 then m is 0 and n is 1, and with the proviso that when m+n is 2 then $R_3$ and $R_4$ are each hydrogen, in an amount sufficient for said treatment.

2. A method according to claim 1 wherein said compound is 5-(3-[(2S)-exobicyclo[2.2.1]hept-2-yloxy]-4-methoxyphenyl)-3,4,5,6-tetrahydropyrimidin-2(1H)-one.

* * * * *